United States Patent [19]

Fujita et al.

[11] 4,263,219
[45] Apr. 21, 1981

[54] PRODUCTION OF SUBSTITUTED PHENYLUREA

[75] Inventors: Fumio Fujita, Osaka; Hiroshi Kishida, Takarazuka; Nobushige Itaya, Nishinomiya; Ichiki Takemoto, Takarazuka, all of Japan

[73] Assignee: Sumitomo Chemical Company, Limited, Osaka, Japan

[21] Appl. No.: 13,610

[22] Filed: Feb. 21, 1979

[30] Foreign Application Priority Data

| | | |
|---|---|---|
| Feb. 21, 1978 [JP] | Japan | 53-19312 |
| Feb. 21, 1978 [JP] | Japan | 53-19313 |
| Feb. 22, 1978 [JP] | Japan | 53-20288 |
| Feb. 22, 1978 [JP] | Japan | 53-20289 |
| Feb. 23, 1978 [JP] | Japan | 53-20493 |
| Feb. 24, 1978 [JP] | Japan | 53-21219 |
| Feb. 24, 1978 [JP] | Japan | 53-21220 |
| Feb. 24, 1978 [JP] | Japan | 53-21221 |
| Feb. 25, 1978 [JP] | Japan | 53-49659 |

[51] Int. Cl.$^3$ .................................. C07C 69/76
[52] U.S. Cl. .................. 260/453 RW; 71/120; 260/500.5 H; 260/453 AR; 564/52; 564/219; 564/305
[58] Field of Search .... 260/553 A, 453 RW, 500.5 H; 71/120

[56] References Cited

U.S. PATENT DOCUMENTS

| | | | |
|---|---|---|---|
| 3,024,283 | 3/1962 | Metcalfe et al. | 260/567.6 M |
| 3,992,432 | 11/1976 | Napier et al. | 260/465.1 |
| 4,004,907 | 1/1977 | Schmid | 71/72 |
| 4,087,272 | 5/1978 | Rohe et al. | 71/120 |
| 4,123,256 | 10/1978 | Yoshida et al. | 71/120 X |
| 4,129,436 | 12/1978 | Takemoto et al. | 71/120 |
| 4,144,049 | 3/1979 | Yoshida et al. | 71/120 |

FOREIGN PATENT DOCUMENTS

950254  2/1964  United Kingdom ............ 260/453 RW

Primary Examiner—Thomas A. Waltz
Attorney, Agent, or Firm—Birch, Stewart, Kolasch and Birch

[57] ABSTRACT

A compound of the formula:

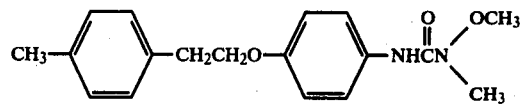

which is useful as a herbicide, is effectively produced by reacting a compound of the formula:

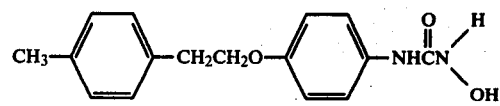

with dimethyl sulfate in a two phase reaction medium consisting of water and a hydrophobic organic solvent in the presence of a phase transfer catalyst, or produced through a novel intermediate of the formula:

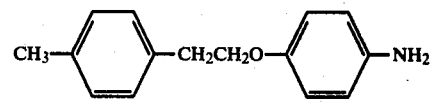

9 Claims, No Drawings

PRODUCTION OF SUBSTITUTED PHENYLUREA

The present invention relates to improvements in the production of a substituted phenylurea. More particularly, it relates to improvements in the production of N'-4-[2-(4-methylphenyl)ethoxy]phenyl-N-methoxy-N-methylurea of the formula:

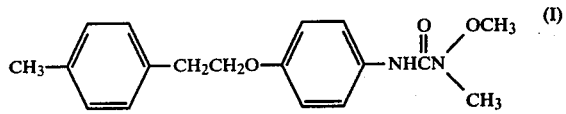

As disclosed in U.S. Pat. No. 4,129,436, the substituted phenylurea (I) has a strong herbicidal activity against many weeds because of its inhibitory action against photosynthesis. Further, it has a high selectivity to cotton, wheat and corn by soil treatment and to rice and soybean by either soil treatment or foliar application.

Among various processes for production of N-methoxy-N-methylurea derivatives, the one comprising the reaction of N-hydroxyurea derivatives with dimethyl sulfate is considered as favorable from the industrial viewpoint [cf. German patent 1,140,925; Angew. Chem., International Ed., Vol. 2, No. 11, 670–673 (1963)]. Application of this process to the production of the substituted phenylurea (I), however, gives the objective compound only in a low yield, and in order to improve the yield, a larger amount of dimethyl sulfate is required. For example, when dimethyl sulfate was used to an amount of 2.5 times per mole with respect to the starting material (i.e. N'-4-[2-(4-methylphenyl)ethoxy]-phenyl-N-hydroxyurea) as described in the said literatures, the yield of the product was 37 to 86% and the purity was 37 to 57%, while when the amount was increased to 4 to 6 times per mole, the yield increased to 80 to 90% but the purity was still 44 to 80%. In the latter case, the reaction conditions such as temperature, pH, reaction medium and reaction time were variously changed, whereby the yield could reach to a considerably high level (e.g. 85 to 99%) but the purity still remained at an insufficient level (e.g. 67 to 82%). Thus, the said known process is disadvantageous in requiring a large amount of dimethyl sulfate, which necessitates the use of a great amount of a base for post-treatment. Further, it requires a purification step which necessitates troublesome the time-consuming operations. In addition, severe control of the reaction conditions is needed for attaining good yields.

In order to overcome the drawbacks present in the said known process, an extensive study has been made, and there is now provided an improved process for production of the substituted phenylurea (I) by reaction of the corresponding hydroxyurea with dimethyl sulfate, which can afford the objective compound in a good yield and a high purity by a simple operation.

Study has also been made to develop the industrially advantageous production of N'-4-[2-(4-methylphenyl)ethoxy]phenyl-N-hydroxyurea of the formula:

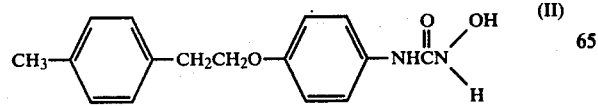

which is the starting material for production of the substituted phenylurea (I). As the result, there are provided various processes for production of the hydroxyurea (II), which are advantageously applicable on an industrial scale.

Accordingly, a basic object of the present invention is to provide an industrially advantageous process for production of the substituted phenylurea (I). Another object of this invention is to provide an improved process for production of the substituted phenylurea (I) from the hydroxyurea (II). A further object of the invention is to provide an improved process for production of the hydroxyurea (II). These and other objects will be apparent to those skilled in the art from the foregoing and subsequent descriptions.

In an aspect of the present invention, there is provided a process for production of the substituted phenylurea (I), which comprises reacting the hydroxyurea (II) with dimethyl sulfate in the presence of a phase transfer catalyst.

In another aspect of this invention, there is provided a process for production of the hydroxyurea (II), which comprises reacting 4-[2-(4-methylphenyl)ethoxy]phenyl isocyanate of the formula:

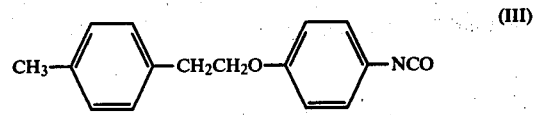

with hydroxylamine, or reacting 4-[2-(4-methylphenyl)ethoxy]phenylcarbamyl chloride of the formula:

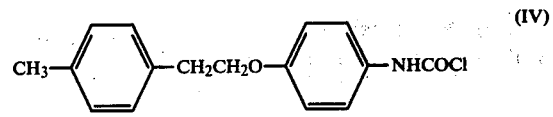

with hydroxylamine.

The phenyl isocyanate (III) is obtainable by heating the phenylcarbamyl chloride (IV), or reacting 4-[2-(4-methylphenyl)ethoxy]aniline of the formula:

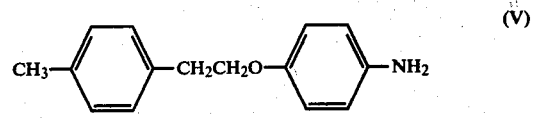

with phosgene or diphosgene. The phenylcarbamyl chloride (IV) is obtainable by reacting the substituted aniline (V) with phosgene or diphosgene.

In a further aspect of the invention, there is provided a process for production of the substituted aniline (V), which comprises reduction of 4-[2-(4-methylphenyl)ethoxy]nitrobenzene of the formula:

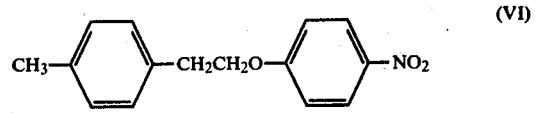

or hydrolysis of 4-[2-(4-methylphenyl)ethoxy]acylanilide of the formula:

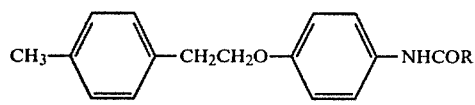 (VII)

wherein R is a hydrogen atom or a lower alkyl group (e.g. methyl, ethyl, propyl, butyl, pentyl).

The substituted nitrobenzene (VI) is obtainable by reacting 2-(4-methylphenyl)ethyl alcohol of the formula:

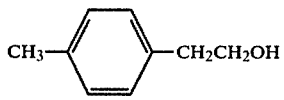 (VIII)

with 4-halonitrobenzene of the formula:

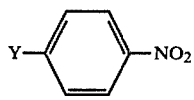 (IX)

wherein Y is a halogen atom (e.g. chlorine, bromine), or reacting 2-(4-methylphenyl)ethyl halide of the formula:

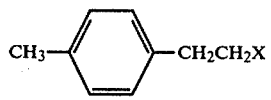 (X)

wherein X is a halogen atom (e.g. chlorine, bromine) with 4-nitrophenol of the formula:

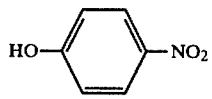 (XI)

The substituted anilide (VII) is obtainable by reducing 4-methyl-α-(4-nitrophenoxy)acetophenone of the formula:

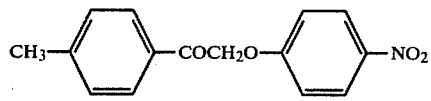 (XII)

in the presence of a lower fatty acid and/or an anhydride thereof, reducing 4-methyl-α-(4-acylaminophenoxy)acetophenone of the formula:

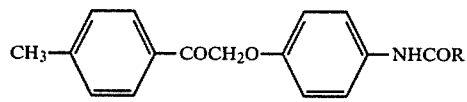 (XIII)

wherein R is as defined above, reducing β-(4-acylaminophenoxy)-α-(4-methylphenyl)ethyl alcohol of the formula:

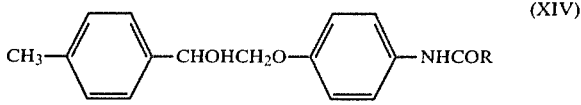 (XIV)

wherein R is as defined above, or reacting 2-(4-methylphenyl)ethyl halide (X) with 4-acylaminophenol of the formula:

 (XV)

wherein R is as defined above.

The nitrophenoxyacetophenone (XII) may be prepared by reacting 4-methylphenacyl halide of the formula:

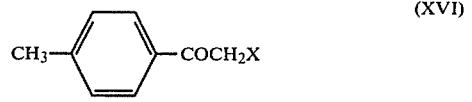 (XVI)

wherein X is as defined above with 4-nitrophenol (XI). The acylaminophenoxyacetophenone (XIII) may be prepared by reducing the nitrophenoxyacetophenone (XII) in the presence of a lower fatty acid and/or an anhydride thereof, or reacting 4-methylphenacyl halide (XVI) with 4-acylaminophenyl (XV). The substituted ethyl alcohol (XIV) may be prepared by reducing the nitrophenoxyacetophenone (XII) in the presence of a lower fatty acid and/or an anhydride thereof, reducing the acylaminophenoxyacetophenone (XIII), or reacting β-halo-α-(4-methylphenyl)ethyl alcohol of the formula:

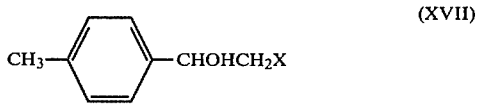 (XVII)

wherein X is as defined above with 4-acylaminophenol (XV), reacting β-halo-β-(4-methylphenyl)ethyl alcohol of the formula:

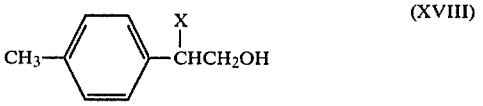 (XVIII)

wherein X is as defined above with 4-acylaminophenol (XV), or reacting 4-methylstyrene oxide of the formula:

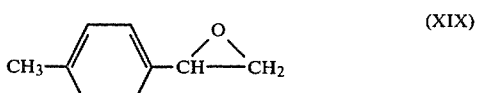 (XIX)

with 4-acylaminophenol (XV).

Some of the intermediates in the above processes are novel and fall within the scope of the invention.

The conversions in the above processes can be inclusively shown in the following scheme:

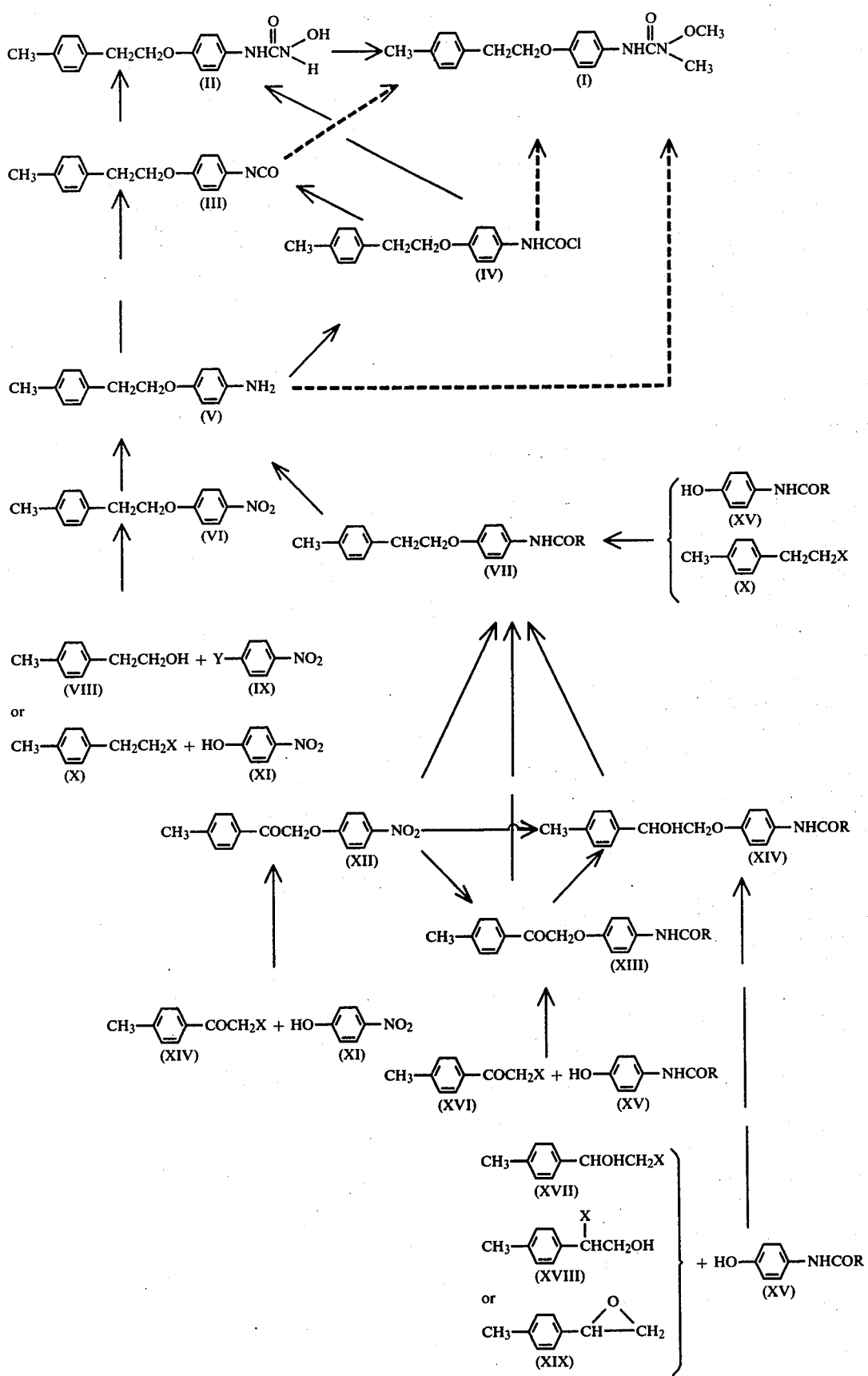
wherein R, X and Y are such as defined above.

1. Production of the substituted phenylurea (I) from the hydroxyurea (II):

The reaction between the hydroxyurea (II) and dimethyl sulfate can be effected in a two-phase reaction medium consisting of water and a hydrophobic organic solvent using a phase transfer catalyst in the presence of absence of a base.

As the phase transfer catalyst, there may be used quaternary ammonium salts (e.g. tetramethylammonium chloride or bromide, tetraethylammonium chloride or bromide, tetra-n-propylammonium chloride or bromide, tetra-n-butylammonium chloride or bromide, lauryltrimethylammonium chloride, trimethyloctadecylammonium chloride, distearyldimethylammonium chloride, laurylpicolinium chloride, stearylamidemethylpyridinium chloride, triethylammonium chloride, diethylpropylbenzylammonium chloride, trimethylbenzylammonium chloride, triethylbenzylammonium chloride or bromide, triethyl-p-chlorobenzylammonium chloride, triethyl-p-methoxybenzylammonium chloride, methylethylpropylbenzylammonium chloride, diethylbutylbenzylammonium chloride, methyldiethylbenzylammonium chloride, dimethylethylbenzylammonium chloride, tripropylbenzylammonium chloride, ethyldipropylammonium chloride, diethyldibenzylammonium chloride, dimethyllaurylbenzylammonium chloride, stearylbenzylmethylammonium chloride, octylbenzyldimethylammonium chloride, myristylbenzyldimethylammonium chloride, tricaprylmethylammonium chloride), phosphonium salts (e.g. tri-n-butylhexadecylphosphonium chloride), etc.

The organic solvent may be, for instance, benzene, toluene, xylene, n-hexane, n-heptane, chlorobenzene, choroform, carbon tetrachloride, methylene chloride, tetrachloroethane or any other hydrophobic organic solvent inert to the reaction.

Examples of the base include alkali metal or alkaline earth metal hydroxides (e.g. sodium hydroxide, potassium hydroxide, calcium hydroxide, magnesium hydroxide), alkali metal or alkaline earth metal carbonates (e.g. sodium carbonate, potassium carbonate, calcium carbonate, magnesium carbonate), etc.

As for the amount of dimethyl sulfate, a theoretical amount to amounts about twice as much are sufficient.

The catalyst displays a sufficient effect within a range of 0.1 to 5% by mole based on the hydroxyurea (II), and a range of 1 to 3% by mole is particularly preferred.

The temperature of this reaction is generally within a range of 0° to 100° C., and a range of 15° to 40° C. is particularly preferred. The reaction time is not particularly limited, but generally it is from 1 to 10 hours.

The method or order by which dimethyl sulfate and the base are added is not particularly limited, but generally the reaction is preferably carried out by adding an aqueous base solution dropwise to the reaction system.

The process of the invention achieves the following technical effects: (1) decrease of the amount of dimethyl sulfate used; (2) lowering of the reaction temperature; (3) shortening of the reaction time; (4) increase of the yield; (5) increase of the purity. In addition, it is advantageous that the reaction can easily proceed to an end without necessity of adjusting pH.

2. Production of the hydroxyurea (II):

The hydroxyurea (II) can easily be produced by reacting the phenyl isocyanate (III) or the phenylcarbamyl chloride (IV) with hydroxylamine.

In this process, hydroxylamine may be used as it is, or, if necessary, it may be produced in situ by the reaction between its salt (e.g. hydrochloride, sulfate) and a base (e.g. sodium hydroxide, potassium hydroxide, sodium carbonate, potassium carbonate). Hydroxylamine is usually employed in an amount of 1 to 3 mole to 1 mole of the phenyl isocyanate (III) or the phenylcarbamyl chloride (IV).

The reaction may be carried out in a solvent inactive to the phenyl isocyanate (III) or the phenylcarbamyl chloride (IV), and examples of the solvent are organic solvents (e.g. benzene, toluene, n-hexane, xylene, dioxane, tetrahydrofuran, pyridine, carbon tetrachloride, dimethylformamide, ethyl ether), water and mixtures thereof.

The reaction temperature is not particularly limited, but generally it is within a range of −20° to 120° C. The reaction time is generally from 10 minutes to 10 hours.

In carrying out the reaction, a catalyst is not particularly necessary when the phenyl isocyanate (III) is the starting material. When the phenylcarbamyl chloride (IV) is the starting material, a hydrogen chloride-acceptor may be added to the reaction system to allow the reaction to proceed smoothly. Examples of the hydrogen chloride-acceptor include tertiary organic amines (e.g. pyridine, triethylamine, quinoline) and inorganic bases (e.g. sodium hydroxide, potassium hydroxide, sodium carbonate, potassium carbonate).

3. Production of the phenyl isocyanate (III) and the phenylcarbamyl chloride (IV):

The benzyl isocyanate (III) can easily be produced by reacting the substituted aniline (V) with phosgene or diphosgene or by heating the phenylcarbamyl chloride (IV) to release hydrogen chloride.

When the substituted aniline (V) is the starting material, the objective compound can be obtained as follows: phosgene or diphosgene is dissolved in a solvent inactive thereto (e.g. benzene, toluene, xylene, chlorobenzene, n-hexane); the substituted aniline (V) is added thereto as such or in solution in the said solvent at −20° to 30° C.; the reaction is effected by elevating the temperature gradually; and the temperature is maintained at 50° to 140° C. for 1 to 10 hours. When the phenylcarbamyl chloride (IV) is the starting material, the objective compound can be obtained by merely heating it in the presence or absence of a solvent. The reaction temperature is not particularly limited and generally may be from 20° to 220° C. The reaction time is usually from a moment to about 10 hours.

The phenylcarbamyl chloride (IV) is obtainable by reacting the substituted aniline (V) with phosgene or diphosgene. In short, this phenylcarbamyl chloride (IV) is possibly an intermediate, through which the phenyl isocyanate (III) is obtained from the substituted aniline (V).

4. Production of the substituted aniline (V):

4-1. Production of the substituted aniline (V) via the substituted nitrobenzene (VI).

(1) Production of the substituted nitrobenzene (VI)

The substituted nitrobenzene (VI) can easily be produced by reacting 2-(4-methylphenyl)ethyl alcohol (VIII) with 4-halonitrobenzene (IX) in the presence of a base, or by reacting 2-(4-methylphenyl)ethyl halide (X) with 4-nitrophenol (XI) in the presence or absence of a base.

The base used in the former reaction may be, for example, alkali metal or alkaline earth metal hydroxides (e.g. sodium hydroxide, potassium hydroxide, calcium hydroxide, magnesium hydroxide), alkali metal or alkaline earth metal carbonates (e.g. sodium carbonate, potassium carbonate, calcium carbonate, magnesium carbonate), metal alcoholates (e.g. potassium tert-butylate), metal hydrides (e.g. sodium hydride, lithium hydride), organic amines (e.g. pyridine, quinoline, diazabicycloudecene (DBU)), alkali metal amides (e.g. sodium amide, lithium amide) and organolithium compounds (e.g. n-butyl lithium). In the latter reaction, metal lower alcoholates (e.g. sodium methylate, sodium ethylate) may be used in addition to the aforesaid bases. Further, a catalyst may be used if necessary in addition to the aforesaid bases. Examples of the catalyst include quaternary ammonium salts (e.g. triethylbenzylammonium chloride, tetraethylammonium bromide) and crown ethers (e.g. dibenzo-18-crown-6, dicyclohexyl-18-crown-6).

4-Nitrophenol (XI) may be used as such or in a salt form. When it is used in a salt form such as the lithium, sodium or potassium salt, the use of the base is not necessary.

As the solvent in the former reaction, there may be used water, alcohols (e.g. tert-butanol), organic polar solvents (e.g. tetrahydrofuran, dimethylsulfoxide (DMSO), dimethylformamide (DMF), organic non-polar slvents (e.g. benzene, toluene, n-hexane, diethyl ether, dimethoxyethane, monochlorobenzene) and mixtures thereof. In the latter reaction, there may be used lower alcohols (e.g. methanol, ethanol, n-propanol, isopropanol, n-butanol), ketones (e.g. acetone, methyl isobutyl ketone), halogenated lower hydrocarbons (e.g. carbon tetrachloride), water and mixtures thereof in addition to the aforesaid solvents.

The reaction temperature depends upon the base and the solvent, but generally it is within a range of $-20°$ to $200°$ C. The reaction time also depends upon the base and the solvent, but generally a range of 10 minutes to about 10 hours is sufficient.

(2) Reduction of the substituted nitrobenzene (VI)

The above prepared substituted nitrobenzene (VI) is subjected to reduction to obtain the substituted aniline (V). The reduction may be carried out in two ways, i.e. catalytic reduction with hydrogen in the presence of a catalyst and reduction with other reducing agents.

(A) Catalytic reduction with hydrogen

Examples of the catalyst usable are palladium, nickel, copper, chromium, platinum, etc. The amount of the catalyst is usually within a range of 0.0001 to 10% by weight based on the substituted nitrobenzene (VI).

The sovent may be methanol, ethanol, water, benzene, dioxane, acetic acid, diethyl ether, tetrahydrofuran or the like. Mixtures of these solvents may be also used if necessary.

The reaction may be carried out at room temperature or with heating under atmospheric or increased pressure. The optimum reaction conditions are determined depending upon the catalyst and the solvent. The reaction time varies with the catalyst, the solvent and the reaction conditions, but generally a range of 30 minutes to about 10 hours is sufficient. Also, an auxiliary such as acids or alkalis may be used in this reaction.

(B) Reduction with other reducing agents

The reduction may be carried out in different ways depending upon the reducing agents. Examples of the reducing agent are a metal (e.g. iron, zinc, tin) or its salt and an acid (e.g. hydrochloric acid, acetic acid); a metal (e.g. iron, zinc) and an alkali; sodium iron, zinc or aluminum amalgam in a neutral condition; a sulfur compound (e.g. sodium sulfide, sodium hydrogen sulfide, hydrogen sulfide, ammonium sulfide, ammonium hydrogen sulfide, sulfur); sodium dithionite; sodium hydrogen sulfite; phenylhydrazine; hydrazine; ammonia, etc.

4-2. Production of the substituted aniline (V) via the substituted anilide (VII).

(1) Production of the substituted anilide (VII) from the nitrophenoxyacetophenone (XII)

The substituted anilide (VII) can be produced very advantageously by catalytic reduction of the nitrophenoxyacetophenone (XII) in the presence of a lower fatty acid and/or an anhydride thereof using a catalyst described hereinafter. In this reduction, the following four reactions proceed in one step: reduction of the nitro group, acylation of the resulting amino group, reduction of the carbonyl group to a hydroxymethylene group and conversion of the hydroxymethylene group to a methylene group. In the course of this reduction, therefore, it may be considered that several kinds of intermediates are formed as shown below:

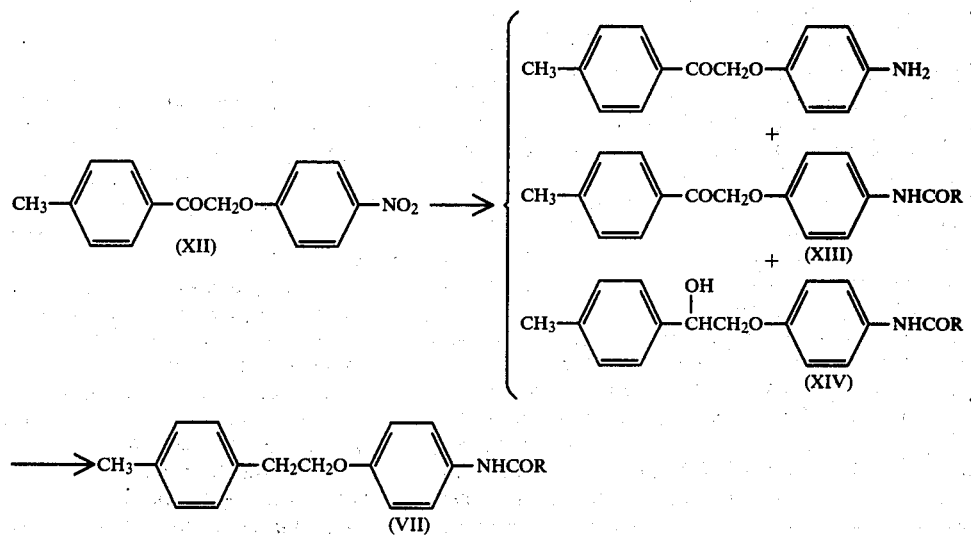

wherein R is as defined above.

The starting nitrophenoxyacetophenone (XII) is obtainable in a quantitative yield, for example, by refluxing an acetone solution containing 4-methylphenacyl halide (XVI) and 4-nitrophenol (XI) in the form of the sodium salt.

In a conventional catalytic reduction, it is well known that a nitro group is very easily reduced, and that a carbonyl group and an alcohol, ester or ether group at the benzyl-position are also easily reduced. In case of the nitrophenoxyacetophenone (XII), however, it was found that the reduction of the carbonyl group into a methylene group does not occur under the conventional condition of catalytic reduction, and that the reduction stops at the stage of benzyl alcohol in many cases. Under the conventional condition of catalytic reduction, the reduction is carried out at room temperature or with heating under and atmospheric or elevated pressure in a solvent (e.g. methanol, ethanol, dioxane, tetrahydrofuran, benzene, water, mixtures thereof) in the presence of a catalyst (e.g. palladium-carbon, platinum oxide, Raney nickel); and if necessary an auxiliary (e.g. hydrochloric acid, sulfuric acid, periodic acid) may be added.

When this reduction is carried out in the presence of a lower fatty acid and/or an anhydride thereof, the carbonyl group at the benzyl-position is rapidly reduced to a methylene group via the alcohol, and the amino group formed at the same time is converted to an acylamino group. This reaction can also be effected in the absence of a lower fatty acid anhydride if a sufficient amount of a lower fatty acid is used and pressure and heat are suitably applied.

The lower fatty acid may be, for instance, formic acid, acetic acid, propionic acid or butyric acid. Its anhydride may be acetic anhydride, propionic anhydride, butyric anhydride or the like. The acid anhydride is preferably used in this reaction, and its amount is 1 to 5 times by mole based on the nitrophenoxyacetophenone (XII). The fatty acid can be used in a great excess to serve as the reaction solvent as well as the reactant.

As the catalyst usable in the reaction, metallic catalysts such as palladium-carbon and platinum oxide may be exemplified. The amount of the catalyst is within a range of 0.0001 to 10% by weight based on the nitrophenoxyacetophenone (XII).

In carrying out the reaction, the lower fatty acid itself may be used as a solvent, but if necessary an organic solvent such as benzene, toluene, xylene, dioxane or tetrahydrofuran may be employed.

If necessary, an auxiliary such as acids or bases (e.g. hydrochloric acid, sulfuric acid, periodic acid, pyridine, triethylamine) may be added to the reaction system.

The reaction temperature is within a range of 20° to 200° C. The reaction pressure is within a range of atmospheric pressure to 100 atm. The reaction time is usually from about 1 to 30 hours.

(2) Production of the substituted anilide (VII) from the acylaminophenoxyacetophenone (XIII)

The substituted anilide (VII) can be produced by reduction of the acylaminophenoxyacetophenone (XIII). The reduction may be carried out in the same manner as above (cf. 4-2 (1)) but in the absence of a lower fatty acid anhydride. Still, alcohols such as methanol and ethanol may be used as the reaction medium in addition to those as exemplified hereinbefore.

(3) Production of the substituted anilide (VII) from the substituted ethyl alcohol (XIV)

The substituted anilide (VII) can be produced by reduction of the substituted ethyl alcohol (XIV). The reduction may be carried out in the same manner as above (cf. 4-2 (1)) but in the absence of a lower fatty acid anhydride. Still, alcohols such as methanol and ethanol may be used as the reaction medium in addition to those as exemplified hereinbefore.

(4) Production of the substituted anilide (VII) by the reaction of 2-(4-methylphenyl)ethyl halide (X) with 4-acylaminophenol (XV)

The substituted anilide (VII) is obtainable by the reaction between 2-(4-methylphenyl)ethyl halide (X) and 4-acylaminophenol (XV). The reaction is usually carried out in the presence of a base in a suitable solvent.

The base and the solvent may be the same as usable in the reaction between 2-(4-methylphenyl)ethyl halide (X) and 4-nitrophenol (XI) as described hereinbefore (cf. 4-1 (1)).

4-Acylaminophenol (XV) can be employed in a free form or a salt form. When used in a salt form such as the lithium, sodium or potassium salt, the use of the base is not necessary.

The reaction temperature depends upon the base and the solvent, but generally it is within a range of $-20°$ to 200° C. The reaction time also depends upon the base and the solvent, but generally a range of about 10 minutes to 10 hours is sufficient.

(5) Hydrolysis of the substituted anilide (VII)

The substituted anilide (VII) obtained by any of the processes as described in (1) to (4) is then subjected to hydrolysis to give the substituted aniline (V). The hydrolysis may be effected by a per se conventional procedure, i.e. by treatment with an acid or a base in a suitable solvent.

Examples of the acid are mineral acids (e.g. hydrochloric acid, sulfuric acid), sulfonic acids (e.g. p-toluenesulfonic acid), etc. Examples of the base are alkali metal hydroxides (e.g. sodium hydroxide, potassium hydroxide), alkaline earth metal hydroxides (e.g. calcium hydroxide, magnesium hydroxide), etc.

As the solvent, water, monoalcohols (e.g. methanol, ethanol, propanol, butanol), dialcohols (e.g. ethylene glycol, diethylene glycol) and mixtures thereof are used preferably.

The reaction temperature varies with the acid or base and the solvent, but generally it is within a range of 0° to 200° C. If necessary, the reaction may be conducted under an elevated pressure. The reaction time varies with the reaction conditions, but generally it takes about 30 minutes to 30 hours.

5. Production of the intermediates for the synthesis of the substituted anilide (VII):

5-1. Production of the nitrophenoxyacetophenone (XII).

The nitrophenoxyacetophenone (XII) can easily be produced by reacting 4-methylphenacyl halide (XVI) with 4-nitrophenol (XI), usually in the presence of a base in a suitable solvent.

The 4-methylphenacyl halide (XVI) usable in this reaction includes 4-methylphenacyl chloride, 4-methylphenacyl bromide and 4-methylphenacyl iodide.

As the base, there may be used alkali metal or alkaline earth metal hydroxides (e.g. sodium hydroxide, potassium hydroxide, calcium hydroxide, magnesium hydroxide), alkali metal or alkaline earth metal carbonates (e.g. sodium carbonate, potassium carbonate, calcium carbonate, magnesium carbonate), metal alcoholates (e.g. sodium methylate, sodium ethylate, potassium tert-butylate), metal hydrides (e.g. sodium hydride, lithium hydride), amines (e.g. pyridine, quinoline, diazabicycloundecene (DBU)), metal amides (e.g. sodium amide, lithium amide), organo-lithium compounds (e.g. n-butyl lithium), etc. 4-Nitrophenol (XI) may be used in a free form or a salt form. When used in a salt form such as the lithium, sodium or potassium salt, the base is not necessary.

As the solvent, there may be employed alcohols (e.g. methanol, ethanol, tert-butanol), organic polar solvents (e.g. acetone, tetrahydrofuran, DMSO, DMF) or organic non-polar solvents (e.g. benzene, toluene, n-hexane, diethyl ether, dimethoxyethane, carbon tetrachloride), or mixtures thereof. If necessary, these solvents may be used in a mixture with water.

The reaction temperature is not particularly limited, but generally it is from 0° to 200° C., preferably the refluxing temperature of the solvent used. The reaction time depends upon the base and the solvent, but generally a range of about 20 minutes to 10 hours is sufficient.

5-2. Production of the acylaminophenoxyacetophenone (XIII).

The acylaminophenoxyacetophenone (XIII) can easily be produced by reacting 4-methylphenacyl halide (XVI) with 4-acylaminophenol (XV) in the presence or absence of a base.

The 4-methylphenacyl halide (XVI) encompasses 4-methylphenacyl chloride, 4-methylphenacyl bromide and 4-methylphenacyl iodide. The acylaminophenol (XV) includes 4-formamidophenol, 4-acetamidophenol, 4-propionamidophenol, etc. The acylaminophenol (XV) may be used in a free form or a salt form.

The base and the solvent usable in this reaction may be the same as used in the reaction between the 4-methylphenacyl halide (XVI) and 4-nitrophenol (XI) as described above (cf. 5-1).

The reaction temperature varies with the base and the solvent, but generally it is within a range of −20° to 200° C. The reaction time also varies with the base and the solvent, but generally it is within a range of about 30 minutes to 15 hours.

5-3. Production of the substituted ethyl alcohol (XIV).

(1) Reduction of the nitrophenoxyacetophenone (XII)

As hereinabove explained (cf. 4-2 (1)), the substituted ethyl alcohol (XIV) is an intermediate in the production of the substituted anilide (VII) from the nitrophenoxyacetophenone (XII) by reduction in the presence of a lower fatty acid and/or an anhydride thereof. Therefore, it is readily obtainable by stopping such reduction at the stage before the conversion of the hydroxymethylene group into a methylene group.

(2) Reduction of the acylaminophenoxyacetophenone (XIII)

Likewise, the substituted ethyl alcohol (XIV) may be considered as an intermediate in the production of the substituted anilide (VII) from the acylaminophenoxyacetopheone (XIII) by reduction. Thus, the reduction in the same manner as above but without using any lower fatty acid anhydride can afford the substituted ethyl alcohol (XIV).

(3) Reaction of β-halo-α-(4-methylphenyl)ethyl alcohol (XVII), β-halo-β-(4-methylphenyl)ethyl alcohol (XVIII) or 4-methylstyrene oxide (XIX) with 4-acylaminophenol (XV)

The reaction is effected in the presence or absence of a base, usually in a suitable solvent. The base and the solvent may be the same as used in the reaction between 4-methylphenacyl halide (XVI) and 4-nitrophenol (XI) (cf. 5-1). 4-Acylaminophenol (XV) may be used in a free form or a salt form.

The reaction temperature depends upon the base and the solvent, but generally it is within a range of −20° to 200° C. Also, the reaction time depends upon the base and the solvent, but generally it is within a range of about 10 minutes to 10 hours.

Still, the phenyl isocyanate (III), the phenylcarbamyl chloride (IV) and the substituted aniline (V) as prepared above may be directly converted into the substituted phenylurea (I) by reacting with N,O-dimethylhydroxylamine, by reacting the N,O-dimethylhydroxylamine and by reacting with N-methyl-N-methoxycarbamyl chloride, respectively.

The present invention will be illustrated in more detail with reference to the following Examples and Comparative Examples, which are not however to be interpreted as limiting the invention thereto.

EXAMPLE 1

To a solution of N'-4-[2-(4-methylphenyl)ethoxy]phenyl-N-hydroxyurea (II) (5.73 g, 0.02 mole) and dimethyl sulfate (5.54 g, 0.044 mole) in toluene (60 ml), tetra-n-butylammonium bromide (0.065 g, 0.0002 mole) was added, and a 10 N aqueous sodium hydroxide solution (4.4 ml, 0.044 mole) was added dropwise thereto at 20° to 22° C. over 30 minutes with stirring. After stirring at the same temperature for 3 hours, the reaction mixture was separated into two layers. The organic layer was washed with water, dried over anhydrous sodium sulfate and concentrated. The residue was dried under reduced pressure to obtain 5.94 g of white crystals. By the melting point, IR and NMR spectra and elemental analytical values as shown below, this product was identified as N'-4-[2-(4-methylphenyl)ethoxy]phenyl-N-methoxy-N-methylurea (I).

Yield: 94.6%.
Purity: 95.0%.
M.P.: 82°–83° C.
IR$\nu_{max}^{nujol}$ cm$^{-1}$: 3320, 1660, 1590, 1500, 1460, 1410, 1380, 1310, 1295, 1260, 1220, 1165, 1110, 1025, 970, 800, 750.
NMR$\delta_{TMS}^{CDCl_3}$: 2.30 (3H, s), 3.00 (2H, t, J=7 Hz), 3.12 (3H, s), 3.70 (3H, s), 4.10 (2H, t, J=7 Hz), 6.73 (2H, d, J=9 Hz), 7.00 (4H, s), 7.24 (2H, d, J=9 Hz), 7.53 (1H, s).

Elementary analysis: Calcd. for $C_{18}H_{22}N_2O_3$: C, 68.77%; H, 7.05%; N, 8.91%. Found: C, 68.83%; H, 7.16%; N, 8.83%.

EXAMPLES 2 TO 6 AND COMPARATIVE EXAMPLE 1

Experimental procedures were similarly carried out using the same starting material as in Example 1. The results are shown in Table 1 together with the result of Comparative Example 1 wherein no catalyst was used.

TABLE 1

| | Example | | | | | Comparative Example 1 |
|---|---|---|---|---|---|---|
| | 2 | 3 | 4 | 5 | 6 | |
| Starting material | N'-4-[2-(4-methylphenyl)-ethoxy]phenyl-N-hydroxyurea (II) | N'-4-[2-(4-methylphenyl)-ethoxy]phenyl-N-hydroxyurea (II) | N'-4-[2-(4-methylphenyl)-ethoxy]phenyl-N-hydroxyurea (II) | N'-4-[2-(4-methylphenyl)-ethoxy]phenyl-N-hydroxyurea (II) | N'-4-[2-(4-methylphenyl)-ethoxy]phenyl-N-hydroxyurea (II) | N'-4-[2-(4-methylphenyl)-ethoxy]phenyl-N-hydroxyurea (II) |
| Dimethyl sulfate/Starting material (molar ratio) | 2.2 | 2.4 | 2.4 | 2.4 | 3 | 4 |
| Catalyst | Tetra-n-butyl-ammonium bromide | Tetra-n-butyl-ammonium bromide | Benzyltri-ethylammonium chloride | Benzyltri-ethylammonium chloride | Tetra-n-butyl-ethylammonium bromide | None |
| Catalyst/Starting material (molar ratio) | 0.005 | 0.01 | 0.01 | 0.02 | 0.01 | — |
| Reaction time (hr) | 3 | 3 | 3 | 3 | 2 | 3 |
| Reaction temperature (°C.) | 20–22 | 20–22 | 20 | 20 | 20 | 20 |
| Yield (%) | 94.6 | 94.6 | 96.7 | 91.4 | 99.6 | 76.3 |
| Purity (%) | 93.8 | 92.5 | 94.1 | 93.3 | 93.7 | 61.9 |

EXAMPLE 7

Hydroxylamine sulfate (8.21 g, 0.05 mole) was dissolved in a mixture of water (50 ml) and toluene (100 ml), and a 10 N aqueous sodium hydroxide solution (9.5 ml, 0.095 mole) was added dropwise thereto at 10° C. over 16 minutes. Thereafter, a solution of 4-[2-(4-methylphenyl)ethoxy]phenyl isocyanate (III) (12.67 g, 0.05 mole) in toluene (50 ml) was added dropwise to the resulting solution at 10° to 12° C. over 2 hours with stirring. After the addition was finished, the reaction mixture was kept at 25° C. for 2 hours. The precipitated crystals were filtered, washed with water and toluene in order and dried under reduced pressure to obtain 14.09 g of white crystals (yield, 98.4%). By the melting point, IR and NMR spectra and elemental analytical values as shown below, this product was identified as N'-4-[2-(4-methylphenyl)ethoxy]phenyl-N-hydroxyurea (II).

M.P.: 167.5° C. (decomp.).

IR$\lambda_{max}^{nujol}$ cm$^{-1}$: 3360, 3195, 1635, 1600, 1540, 1510, 1455, 1380, 1245, 1030, 820, 800.

NMR$\delta_{TMS}^{D6-DMSO}$: 2.22 (3H, s), 2.90 (2H, t, J=7 Hz), 4.03 (2H, t, J=7 Hz), 6.68 (2H, d, J=9 Hz), 7.00 (4H, s), 7.33 (2H, d, J=9 Hz), 8.40 (1H, s), 8.49 (1H, s), 8.67 (1H, s).

Elementary analysis: Calcd. for $C_{16}H_{13}N_2O_3$: C, 67.11%; H, 6.34%; N, 9.78%. Found: C, 67.40%; H, 6.49%; N, 9.69%.

EXAMPLE 8

To a toluene solution of hydroxylamine prepared from hydroxylamine hydrochloride (6.95 g, 0.1 mole) and a 10 N aqueous sodium hydroxide solution (9.5 ml, 0.095 mole), pyridine (4.74 g, 0.06 mole) was dissolved, and a solution of 4-[2-(4-methylphenyl)ethoxy]phenylcarbamyl chloride (IV) (14.5 g, 0.05 mole) in toluene (60 ml) was added dropwise thereto at 15° to 20° C. over 1 hour. Thereafter, the reaction mixture was heated to 60° C. for 4 hours with stirring, and after cooling, water was added thereto. The precipitated crystals were filtered, washed with water and toluene in order and recrystallized from acetone to obtain 13.8 g of N'-4-[2-(4-methylphenyl)ethoxy]phenyl-N-hydroxyurea (II) as white crystals (yield, 96.4%). The melting point and IR and NMR spectra agreed completely with those in Example 7.

EXAMPLE 9

4-[2-(4-Methylphenyl)ethoxy]aniline (V) (19.3 g, 0.085 mole) was dissolved in toluene (230 ml), and the resulting solution was added dropwise to a solution of phosgene (12.6 g, 0.13 mole) in toluene (40 ml) at room temperature over 20 minutes. The mixture was slowly heated to 90° C. in 1 hour. After removing the solvent by evaporation, the residue was distilled under reduced pressure to obtain 20.7 g of white crystals (yield, 96.4%). By the melting point, boiling point, IR and NMR spectra and elemental analytical values as shown below, this product was identified as 4-[2-(4-methylphenyl)ethoxy]phenyl isocyanate (III).

M.P.: 35°–36° C.

B.P.: 180°190° C./1.0 mmHg.

IR$\nu_{max}^{nujol}$ cm$^{-1}$: 2150, 1350, 1200, 1140, 1000, 650.

NMR$\delta_{TMS}^{CCL4}$: 2.22 (3H, s), 2.89 (2H, t, J=8 Hz), 3.91 (2H, t, J=8 Hz), 6.65 (4H, doubled), 6.90 (4H, s).

Elementary analysis: Calcd. for $C_{16}H_{13}NO_2$: C, 75.87%; H, 5.97%, N. 5.53%. Found: C, 76.01%; H, 5.91%; N, 5.40%.

EXAMPLE 10

The procedure was carried out in the same manner as in Example 9 except that diphosgene (19.8 g, 0.1 mole) was used in place of phosgene. Thus, 19.5 g of 4-[2-(4-methylphenyl)ethoxy]phenyl isocyanate (III) were obtained as white crystals (yield, 90.7%). B.P., 131°–133° C./0.07 mmHg.

The IR and NMR spectra and gas chromatogram of this product agreed completely with those in Example 9.

EXAMPLE 11

A solution of 4-[2-(4-methylphenyl)ethoxy]phenylcarbamyl chloride (IV) (14.4 g, 0.05 mole) in toluene (80 ml) was heated at 60° C. for 1 hour and distilled under reduced pressure to obtain 12 g of 4-[2-(4-methylphenyl)ethoxy]phenyl isocyanate (III) as white crystals (yield, 94.9%). B.P., 170°–181° C./0.9 mmHg.

The IR and NMR spectra and gas chromatogram of this product agreed completely with those in Example 9.

EXAMPLE 12

2-(4-Methylphenyl)ethyl alcohol (VIII) (13.6 g, 0.1 mole), 4-nitrochlorobenzene (IX: X=Cl) (15.8 g, 0.1 mole) and powdery potassium hydroxide (8.4 g, 0.15 mole) were added to dimethylformamide (150 ml), followed by stirring at 25° C. for 10 hours. The reaction mixture was poured into ice water, and the precipitated crystals were filtered and recrystallized from 95% ethanol. Yield, 20 g (78%).

From the IR and NMR spectra and elemental analytical values shown below, this product was identified as 4-[2-(4-methylphenyl)ethoxy]nitrobenzene (VI).

B.P.: 190°–195° C./0.3 mmHg.
M.P.: 56°–57° C.
IR$\nu_{max}^{nujol}$ cm$^{-1}$: 1595, 1500, 1460, 1340, 1260, 1105, 1015, 850, 760.
NMR$\delta_{TMS}^{CDCl_3}$: 2.31 (3H, s), 3.06 (2H, t, J=7 Hz), 4.22 (2H, t, J=7 Hz), 6.90 (2H, d, J=9 Hz), 7.15 (4H, s), 8.15 (2H, d, J=9 Hz).
Elementary analysis: Calcd. for $C_{15}H_{15}NO_3$: C, 70.02%; H, 5.88%; N, 5.44%. Found: C, 70.30%; H, 5.96%; N, 5.35%.

EXAMPLE 13

A mixture of 2-(4-methylphenyl)ethyl alcohol (VIII) (13.6 g, 0.1 mole), 4-nitrochlorobenzene (IX: X=Cl) (15.8 g, 0.1 mole), toluene (92 g), tetra-n-butylammonium bromide (3.2 g, 0.01 mole) and a 50% aqueous sodium hydroxide solution (24 g) was stirred vigorously at 50° to 60° C. for 5 hours. The organic layer was separated, washed with water two times and then concentrated in vacuo. By recrystallizing the crude product from 95% ethanol, 20.6 g (yield, 80%) of 4-[2-(4-methylphenyl)ethoxy]nitrobenzene (VI) were obtained as white crystals.

The IR, NMR and gas chromatogram were in agreement with those of Example 12.

EXAMPLE 14

To a solution of 65% sodium hydride (1.1 g, 0.03 mole) in dimethylsulfoxide (30 ml) were added 2-(4-methylphenyl)ethyl alcohol (VIII) (2.72 g, 0.02 mole) and 4-nitrochlorobenzene (IX: X=Cl) (3.15 g, 0.02 mole). After heating to 30° C. for 5 hours with stirring, the reaction mixture was treated in the same manner as in Example 12 to obtain 4.6 g of 4-[2-(4-methylphenyl)ethoxy]nitrobenzene (VI) as white crystals (yield, 89.5%).

The IR and NMR spectra and gas chromatogram of this product agreed completely with those in Example 12.

EXAMPLE 15

2-(4-Methylphenyl)ethyl alcohol (VIII) (2.72 g, 0.02 mole), 4-nitrochlorobenzene (IX: X=Cl) (3.15 g, 0.02 mole) and potassium hydroxide (1.4 g, 0.025 mole) were added to benzene (60 ml), and dicyclohexyl-18-crown-6 (0.2 g) was added thereto, followed by reaction at 60° C. for 10 hours. The reaction mixture was washed with water and concentrated, and the precipitated crystals were recrystallized from 95% ethanol to obtain 4.5 g of 4-[2-(4-methylphenyl)ethoxy]nitrobenzene (VI) as white crystals (yield, 87.5%).

The IR and NMR spectra and gas chromatogram of this product agreed completely with those in Example 12.

EXAMPLE 16

2-(4-Methylphenyl)ethyl bromide (X: X=Br) (10 g, 0.05 mole) and sodium 4-nitrophenolate (XI) (8.1 g, 0.05 mole) were added to dimethylformamide (60 ml), and the mixture was reacted at 90° C. for 5 hours. Thereafter, the reaction mixture was treated in the same manner as in Example 12 to obtain 9.5 g of 4-[2-(4-methylphenyl)ethoxy]nitrobenzene (VI) as white crystals (yield, 73.9%).

The IR and NMR spectra and gas chromatogram of this product agreed completely with those in Example 12.

EXAMPLE 17

4-[2-(4-Methylphenyl)ethoxy]nitrobenzene (VI) (5.14 g, 0.02 mole) was dissolved in a mixture of 95% ethanol (30 ml) and benzene (30 ml). This solution was subjected to catalytic reduction with 10% palladium-carbon (0.1 g) for 4 hours, during which 1750 ml of hydrogen was absorbed. The catalyst was removed by filtration, and the filtrate was concentrated to obtain 4.9 g of crystals. The crystals were recrystallized from a mixture of benzene and n-hexane to obtain 4.3 g of pale yellow crystals (yield, 95%). By the melting point, boiling point, IR and NMR spectra and elemental analytical values as shown below, this product was identified as 4-[2-(4-methylphenyl)ethoxy]aniline (V).

M.P.: 65°–66° C.
B.P.: 150°–161° C./0.4 mmHg.
IR$\nu_{max}^{nujol}$ cm$^{-1}$: 3360, 3280, 1510, 1240, 1030, 830, 810.
NMR$\delta_{TMS}^{CDCl_3}$: 2.30 (3H, s), 2.98 (2H, t, J=7 Hz), 3.26 (2H, s), 4.04 (2H, t, J=7 Hz), 6.65 (4H, double, d), 7.12 (4H, s).
Elementary analysis: Calcd. for $C_{15}H_{17}NO$: C, 79.26%; H, 7.54%; N, 6.16%. Found: C, 79.04%; H, 7.62%; N, 6.33%.

EXAMPLE 18

4-[2-(4-Methylphenyl)ethoxy]nitrobenzene (VI) (5.14 g, 0.02 mole) and iron powder (6.7 g, 0.12 mole) were added to 50% aqueous ethanol (50 ml), and a solution of conc. hydrochloric acid (1 ml) in 50% aqueous ethanol (10 ml) was added dropwise thereto over 15 minutes with stirring under reflux. After heating under reflux for an additional 2 hours, the reaction mixture was cooled, neutralized with a dilute aqueous sodium hydroxide solution and extracted with ether. The ether layer was washed with water, dried over anhydrous potassium carbonate, concentrated and distilled to obtain 4.1 g of 4-[2-(4-methylphenyl)ethoxy]aniline (V) (yield, 90.3%).

The IR and NMR spectra and gas chromatogram of this product agreed completely with those in Example 17.

EXAMPLE 19

4-[2-(4-Methylphenyl)ethoxy]nitrobenzene (VI) (5.14 g, 0.02 mole), sodium hydroxide powder (3.0 g) and sulfur (1.6 g, 0.05 mole) were added to a mixture of acetone (20 ml) and methanol (20 ml), followed by heating under reflux for 5 hours. After cooling, the reaction mixture was diluted with water, extracted with ether and treated in the same manner as in Example 18 to obtain 4.4 g of 4-[2-(4-methylphenyl)ethoxy]aniline (V) (yield, 96.9%).

The IR and NMR spectra and gas chromatogram of this product agreed completely with those in Example 17.

EXAMPLE 20

4-[2-(4-Methylphenyl)ethoxy]nitrobenzene (VI) (5.14 g, 0.02 mole) and sodium sulfide nonahydrate (9.6 g, 0.04 mole) were added to a mixture of 95% aqueous ethanol (50 ml) and 29% aqueous ammonia (50 ml), followed by heating under reflux for 20 hours. Sulfur deposited was filtered while hot, and the filtrate was cooled, extracted with ether and treated in the same manner as in Example 17 to obtain 4.3 g of 4-[2-(4-methylphenyl)ethoxy]aniline (V) (yield, 95%).

The IR and NMR spectra and gas chromatogram of this product agreed completely with those in Example 17.

EXAMPLE 21

Acetic anhydride (20 g, 0.2 mole) and 10% palladium-carbon (1 g) were added to a solution of 4-methyl-α-(4-nitrophenoxy)acetophenone (XII) (27.1 g, 0.1 mole) in acetic acid (500 ml), and catalytic reduction was carried out while passing hydrogen through the solution at 50° C. The reaction was stopped after 8 hours, and by that time 20.5 liters of hydrogen was adsorbed. After removing the catalyst by filtration, acetic acid was removed under reduced pressure to obtain a white powder. The powder was recrystallized from ethanol to obtain 21 g of white crystals (yield, 78.1%). By the melting point, IR and NMR spectra and elemental analytical values as shown below, this product was identified as 4-[2-(4-methylphenyl)ethoxy]acetanilide (VII: R=CH$_3$).

M.P.: 130°–132° C.

IR$\nu_{max}^{nujol}$ cm$^{-1}$: 3270, 1655, 1535, 1510, 1460, 1380, 1270, 1250, 1030, 825, 810.

NMR$\delta_{TMS}^{CDCl_3}$: 2.05 (3H, s), 2.30 (3H, s), 2.98 (2H, t, J=7 Hz), 4.06 (2H, t, J=7 Hz), 6.75 (2H, d, J=9 Hz), 7.10 (4H, s), 7.33 (2H, d, J=9 Hz), 7.82 (1H, broad s).

Elementary analysis: Calcd. for C$_{17}$H$_{19}$NO$_2$: C, 75.81%; H, 7.11%; N, 5.20%. Found: C, 75.97%; H, 7.03%; N, 5.15%.

EXAMPLE 22

4-Methyl-α-(4-nitrophenoxy)acetophenone (XII) (2.71 g, 0.01 mole), 10% palladium-carbon (0.2 g) and acetic acid (50 ml) were charged in an autoclave, and the atmosphere in the autoclave was replaced with 28 kg/cm$^2$ of hydrogen. After raising the temperature gradually, the reaction mixture was kept at 100° C. for 8 hours with stirring. Thereafter, the reaction mixture was cooled and treated in the same manner as in Example 21 to obtain 2.2 g of 4-[2-(4-methylphenyl)ethoxy]acetanilide (VII: R=CH$_3$) as white crystals (yield, 81.8%).

The melting point, IR and NMR spectra and gas chromatogram of this product agreed completely with those in Example 21.

EXAMPLE 23

10% Palladium-carbon (0.2 g) was added to a solution of 4-methyl-α-(4-acetamidophenoxy)acetophenone (XIII: R=CH$_3$) (2.83 g, 0.01 mole) in acetic acid (50 ml), and catalytic reduction was carried out while passing hydrogen therethrough at 50° C. under atmospheric pressure for 5 hours. During that time, 605 ml of hydrogen was absorbed. The reaction mixture was treated in the same manner as in Example 21 to obtain 2.35 g of 4-[2-(4-methylphenyl)ethoxy]acetanilide (VII: R=CH$_3$) as white crystals (yield, 87.4%).

The melting point, IR and NMR spectra and gas chromatogram of this product agreed completely with those in Example 21.

EXAMPLE 24

10% Palladium-carbon (0.2 g) was added to a solution of β-(4-acetamidophenoxy)-α-(4-methylphenyl)ethyl alcohol (XIV: R=CH$_3$) (2.85 g, 0.01 mole) in acetic acid (50 ml), and hydrogen was passed therethrough at 45° C. under atmospheric pressure for 4 hours. During that time, 400 ml of hydrogen was absorbed. The reaction mixture was then treated in the same manner as in Example 21 to obtain 2.03 g of 4-[2-(4-methylphenyl)ethoxy]acetanilide (VII: R=CH$_3$) as white crystals (yield, 75.5%).

The melting point, IR and NMR spectra and gas chromatogram of this product agreed completely with those in Example 21.

EXAMPLE 25

Sodium methylate (3.24 g, 0.06 mole), 4-methylphenethyl bromide (X: X=Br) (10 g, 0.05 mole) and 4-acetamidophenol (XV: R=CH$_3$) (7.6 g, 0.05 mole) were added to methanol (80 ml), and the mixture was heated to 40° C. for 6 hours with stirring. After cooling, the solvent was removed under reduced pressure, and water was added to the residue, followed by extraction with ether. The ether layer was washed with water, dried over anhydrous magnesium sulfate and concentrated to obtain 12.3 g of 4-[2-(4-methylphenyl)ethoxy]acetanilide (VII: R=CH$_3$) as white crystals (yield, 91.4%).

The melting point, IR and NMR spectra and gas chromatogram of this product agreed completely with those in Example 21.

EXAMPLE 26

To a mixture of 4-[2-(4-methylphenyl)ethoxy]acetanilide (VII: R=CH$_3$) (2.69 g, 0.01 mole) and 95% ethanol (20 ml) was added dropwise conc. hydrochloric acid (4 ml) over 15 minutes with stirring under reflux. Heating was continued for an additional 4 hours. After cooling, the reaction mixture was neutralized with an aqueous dilute sodium hydroxide solution, extracted with ether and treated in the same manner as in Example 17 to obtain 2.0 g of 4-[2-(4-methylphenyl)ethoxy]aniline (V) (yield, 88.2%).

The IR and NMR spectra and gas chromatogram of this product agreed completely with those in Example 17.

EXAMPLE 27

4-[2-(4-Methylphenyl)ethoxy]acetanilide (VII: R=CH$_3$) (2.69 g, 0.01 mole) and sodium hydroxide (1 g, 0.025 mole) were added to ethylene glycol (20 ml), and the mixture was heated at 130° C. for 3 hours with stirring. After cooling, the reaction mixture was diluted with water, extracted with ether and treated in te same manner as in Example 17 to obtain 2.1 g of 4-[2-(4-methylphenyl)ethoxy]aniline (V) (yield, 92.5%).

The IR and NMR spectra and gas chromatogram of this product agreed completely with those in Example 17.

EXAMPLE 28

4-[2-(4-Methylphenyl)ethoxy]acetanilide (VII: R=CH$_3$) (2.69 g, 0.01 mole) and sodium hydroxide (1 g, 0.025 mole) were added to 95% ethanol (20 ml), and the mixture was heated under reflux at 80° C. for 24 hours. Thereafter, the reaction mixture was treated in the same manner as in Example 27 to obtain 2.1 g of 4-[2-(4-methylphenyl)ethoxy]aniline (V) (yield, 92.5%).

The IR and NMR spectra and gas chromatogram of this product agreed completely with those in Example 17.

EXAMPLE 29

4-Methylphenacyl bromide (XVI: X=Br) (76.7 g, 0.36 mole) and sodium 4-nitrophenolate dihydrate (XI) (70.9 g, 0.36 mole) were added to acetone (500 ml), and the mixture was heated under reflux for 4 hours. After cooling, the solvent was removed under reduced pressure, and water was added to dissolve the produced inorganic salt. The precipitate was filtered and recrystallized from a mixture of acetone, ethanol and benzene to obtain 92.2 g of crystals (yield, 94.5%). From the IR and NMR spectra, this product was identified as 4-methyl-α-(4-nitrophenoxy)acetophenone (XII).

M.P.: 160°-161° C.

IR$\nu_{max}^{nujol}$ cm$^{-1}$: 1695, 1595, 1450, 1340, 1230, 1105, 970, 840, 800.

NMR$\delta_{TMS}^{CDCl_3}$: 2.40 (3H, s), 5.36 (2H, s), 6.94 (2H, d, J=9 Hz), 7.30 (2H, d, J=8 Hz), 7.84 (2H, d, J=8 Hz), 8.15 (2H, d, J=9 Hz).

EXAMPLE 30

4-Methylphenacyl chloride (XVI: X=Cl) (37.8 g, 0.224 mole) and sodium 4-nitrophenolate (XI) (38.6 g, 0.24 mole) were added to acetone (300 ml), and the mixture was heated under reflux for 10 hours. Thereafter, the reaction mixture was treated in the same manner as in Example 29 to obtain 47.9 g of 4-methyl-α-(4-nitrophenoxy)acetophenone (XII) (yield, 78.9%).

The IR and NMR spectra and gas chromatogram of this product agreed completely with those in Example 29.

EXAMPLE 31

4-Methylphenacyl bromide (XVI: X=Br) (63 g, 0.296 mole), 4-nitrophenol (XI) (42.4 g, 0.305 mole) and potassium hydroxide (22.5 g, 0.4 mole) were added to methanol (300 ml), and the mixture was heated under reflux for 4 hours. Thereafter, the reaction mixture was treated in the same manner as in Example 29 to obtain 50.0 g of 4-methyl-α-(4-nitrophenoxy)acetophenone (XII) (yield, 62.3%).

The IR and NMR spectra and gas chromatogram of this product agreed completely with those in Example 29.

EXAMPLE 32

4-Methylphenacyl bromide (XVI: X=Br) (10 g, 0.047 mole), 4-acetamidophenol (XV: R=CH$_3$) (7.6 g, 0.05 mole) and anhydrous potassium carbonate (8.3 g, 0.06 mole) were added to acetone (200 ml), and the mixture was heated under reflux for 6 hours. After cooling, the solvent was removed under reduced pressure, and water was added to the residue, followed by extraction with ether. The ether layer was washed with an aqueous dilute sodium hydroxide solution and an aqueous sodium chloride solution in order, dried over anhydrous magnesium sulfate and concentrated to obtain a white solid. By recrystallization from acetone, 12.4 g of white crystals was obtained (yield, 98.2%).

By the melting point, IR and NMR spectra and elemental analytical values as shown below, this product was identified as 4-methyl-α-(4-acetamidophenoxy)acetophenone (XIII: R=CH$_3$).

M.P.: 155°-156° C.

IR$\nu_{max}^{nujol}$ cm$^{-1}$: 3300, 1670, 1600, 1550, 1510, 1260, 1225, 1175, 1080, 980, 820, 800.

NMR$\delta_{TMS}^{D6-DMSO}$: 2.03 (3H, s), 2.40 (2H, s), 5.27 (2H, s), 6.75 (2H, d, J=9 Hz), 7.20 (2H, d, J=8 Hz), 7.38 (2H, d, J=8 Hz), 7.77 (2H, d, J=9 Hz), 9.40 (1H, broad s).

Elementary analysis: Calcd. for C$_{17}$H$_{17}$NO$_3$: C, 72.06%; H, 6.05%; N, 4.94%. Found: C, 72.15%; H, 6.09%; N, 4.98%.

EXAMPLE 33

4-Methylphenacyl chloride (XVI: X=Cl) (8.4 g, 0.05 mole), 4-acetamidophenol (XV: R=CH$_3$) (7.6 g, 0.05 mole) and anhydrous potassium carbonate (8.3 g, 0.06 mole) were added to acetone (200 ml), and the mixture was heated under reflux for 12 hours. Thereafter, the reaction mixture was treated in the same manner as in Example 32 to obtain 11.7 g of 4-methyl-α-(4-acetamidophenoxy)acetophenone (XIII: R=CH$_3$) as white crystals (yield, 82.7%).

The melting point, IR and NMR spectra and gas chromatogram of this product agreed completely with those in Example 32.

EXAMPLE 34

65% Sodium hydride (2.2 g, 0.06 mole) was added to dimethylsulfoxide (60 ml), and a solution of 4-acetamidophenol (XV: R=CH$_3$) (7.6 g, 0.05 mole) in dimethylsulfoxide (20 ml) was dropwise added thereto. After cooling to 5° to 10° C., a solution of 4-methylphenacyl chloride (XVI: X=Cl) (8.4 g, 0.05 mole) in dimethylsulfoxide (20 ml) was added dropwise thereto over 1 hour. Thereafter the reaction was carried out at 15° C. for 8 hours. The reaction mixture was diluted with water, and the precipitated crystals were filtered and recrystallized from acetone to obtain 7.9 g of 4-methyl-α-(4-acetamidophenoxy)acetophenone (XIII: R=CH$_3$) as white crystals (yield, 55.8%).

The melting point, IR and NMR spectra and gas chromatogram of this product agreed completely with those in Example 32.

EXAMPLE 35

4-Methyl-α-(4-nitrophenoxy)acetophenone (XII) (13.6 g, 0.05 mole) and acetic anhydride (7.14 g, 0.07 mole) were dissolved in acetic acid (150 ml). After adding 10% palladium-carbon (0.1 g) thereto, hydrogen (6.4 liters) was absorbed at 35° to 50° C. over 8 hours. The catalyst was removed by filtration, and acetic acid was removed under reduced pressure to obtain 14.7 g of a white solid. The solid was recrystallized from ethanol to obtain 12.5 g of white crystals (yield, 87.7%). By the melting point, IR and NMR spectra and elemental analytical values as shown below, this product was identified β-(4acetamidophenoxy)-β-(4-methylphenyl)ethyl alcohol (XIV: R=CH$_3$).

M.P.: 148°-149.5° C.

IR$\nu_{max}^{nujol}$ cm$^{-1}$: 3280, 3260, 1650, 1600, 1540, 1520, 1305, 1250, 1040, 825, 805.

NMR δ$_{TMS}^{D6-DMSO}$: 2.00 (3H, s), 2.28 (3H, s), 3.8–4.1 (2H, m), 4.70–5.0 (1H, m), 5.50 (1H, broad s), 6.7–7.7 (8H, m), 9.75 (1H, s).

Elementary analysis: Calcd. for $C_{17}H_{19}NO_3$: C, 71.56%; H, 6.71%; N, 4.91%. Found: C, 71.44%; H, 6.78%; N, 4.97%.

EXAMPLE 36

10% Palladium-carbon (0.1 g) was added to a solution of 4-methyl-α-(4-acetamidophenoxy)acetophenone (XIII: R=CH$_3$) (2.83 g, 0.01 mole) in ethanol (50 ml), and catalytic reduction was carried out at 25° C. for 2 hours during which 290 ml of hydrogen was absorbed. After removing the catalyst by filtration, after-treatment was carried out in the same manner as in Example 35 to obtain 2.55 g of β-(4-acetamidophenoxy)-α-(4-methylphenyl)ethyl alcohol (XIV: R=CH$_3$) as white crystals (yield, 89.5%).

The melting point, IR and NMR spectra and gas chromatogram of this product agreed completely with those in Example 35.

EXAMPLE 37

To a mixture of 65% sodium hydride (4.4 g, 0.12 mole) and dimethylsulfoxide (60 ml) was added dropwise a solution of 4-acetamidophenol (XV: R=CH$_3$) (15.1 g, 0.1 mole) in dimethylsulfoxide (30 ml). After cooling the resulting mixture to 8° to 10° C., a solution of 4-methylstyrene oxide (XIX) (13.4 g, 0.1 mole) in dimethylsulfoxide (30 ml) was added dropwise thereto over 1 hour, followed by reaction at 15° C. for 4 hours. Water was added to the reaction solution, and the precipitated crystals were filtered and recrystallized from ethanol to obtain 17.5 g of β-(4-acetamidophenoxy)-α-(4-methylphenyl)ethyl alcohol (XIV: R=CH$_3$) as white crystals (yield, 61.4%).

The melting point, IR and NMR spectra and gas chromatogram of this product agreed completely with those in Example 35.

What is claimed is:

1. A process for producing N'-4-[2-(4-methylphenyl)ethoxy]phenyl-N-methoxy-N-methylurea of the formula:

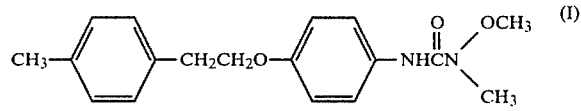

which comprises reacting N'-4-[2-(4-methylphenyl)ethoxy]phenyl-N-hydroxyurea of the formula:

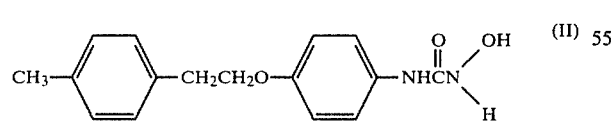

with dimethyl sulfate in the presence of a phase transfer catalyst.

2. The process according to claim 1, wherein the phase transfer catalyst is a member selected from the group consisting of quaternary ammonium salts and phosphonium salts.

3. The process according to claim 1, wherein the reaction is carried out in a two phase reaction medium consisting of water and a hydrophobic organic solvent.

4. The process according to claim 1, wherein the reaction is carried out in the presence of a base.

5. The process according to claim 1, wherein the dimethyl sulfate is used in a stoichiometric amount to about two times the amount thereof.

6. The process according to claim 1, wherein the phase transfer catalyst is used in an amount of 0.1 to 5 mole % based on the hydroxyurea (II).

7. The process according to claim 1, wherein the reaction is carried out at a temperature of 0° to 100° C.

8. A process for producing N'-4-[2-(4-methylphenyl)ethoxy]phenyl-N-methoxy-N-methylurea of the formula:

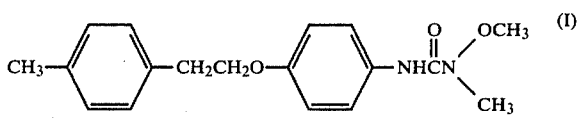

which comprises reacting 4-[2-(4-methylphenyl)ethoxy]aniline of the formula:

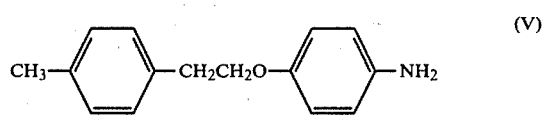

with phosgene or diphosgene, reacting the resulting 4-[2-(4-methylphenyl)ethoxy]phenylcarbamyl chloride of the formula:

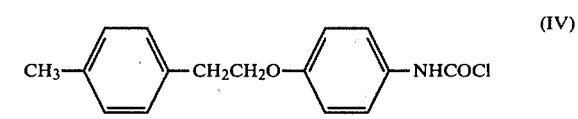

with hydroxylamine and reacting the resulting N'-4-[2-(4-methylphenyl)ethoxy]phenyl-N-hydroxyurea of the formula:

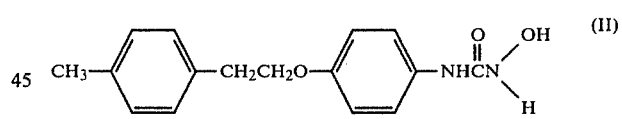

with dimethyl sulfate in the presence of a phase transfer catalyst.

9. A process for producing N'-4-[2-(4-methylphenyl)ethoxy]phenyl-N-methoxy-N-methylurea of the formula:

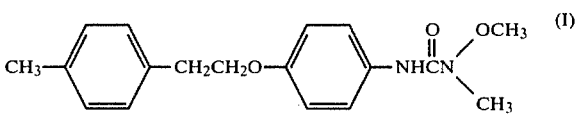

which comprises reacting 2-(4-methylphenyl)ethyl alcohol of the formula:

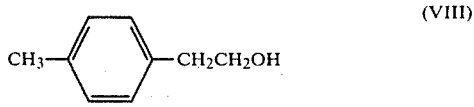

with 4-halonitrobenzene of the formula:

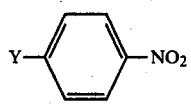

wherein Y is a halogen atom or a 2-(4-methylphenyl)ethyl halide of the formula:

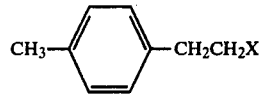

wherein X is a halogen atom with 4-nitrophenol of the formula:

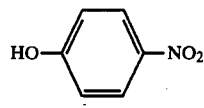

, reacting 4-[2-(4-methylphenylethoxy]aniline of the formula:

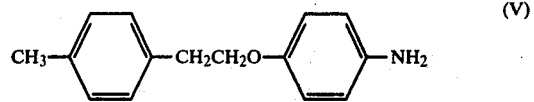

with phosgene or diphosgene, reacting the resulting 4-[2-(4-methylphenyl)ethoxy]phenylcarbamyl chloride of the formula:

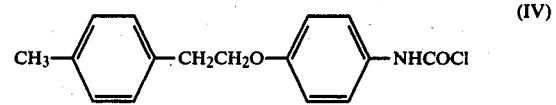

with hydroxylamine and reacting the resulting N'-4-[2-(4-methylphenyl)ethoxy]phenyl-N-hydroxyurea of the formula:

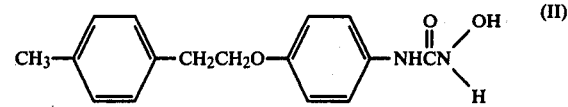

with dimethyl sulfate in the presence of a phase transfer catalyst.

* * * * *

UNITED STATES PATENT AND TRADEMARK OFFICE
CERTIFICATE OF CORRECTION

PATENT NO. : 4,263,219
DATED : April 21, 1980
INVENTOR(S) : Fujita et al

It is certified that error appears in the above—identified patent and that said Letters Patent is hereby corrected as shown below:

In the heading entitled "[30] Foreign Application Priority Data", change "Feb. 25, 1978 [JP] Japan .... 53-49659" to --Apr. 25, 1978 [JP] Japan .... 53-49659--

Signed and Sealed this

First Day of September 1981

[SEAL]

Attest:

Attesting Officer

GERALD J. MOSSINGHOFF
Commissioner of Patents and Trademarks